United States Patent [19]

Kaetsu et al.

[11] 4,272,617
[45] Jun. 9, 1981

[54] IMMOBILIZATION OF ENZYMES OR BACTERIA CELLS

[75] Inventors: Isao Kaetsu; Minoru Kumakura; Masaru Yoshida, all of Takasaki, Japan

[73] Assignee: Japan Atomic Energy Research Institute, Tokyo, Japan

[21] Appl. No.: 60,867

[22] Filed: Jul. 26, 1979

Related U.S. Application Data

[63] Continuation of Ser. No. 765,604, Feb. 4, 1977, abandoned.

[30] Foreign Application Priority Data

Feb. 9, 1976 [JP] Japan .................................. 51-13083

[51] Int. Cl.³ .............................................. C12N 11/04
[52] U.S. Cl. ................................................... 435/182
[58] Field of Search ................ 435/174, 177, 182, 181

[56] References Cited

U.S. PATENT DOCUMENTS

| 3,860,490 | 1/1975 | Guttag ................................. 435/182 |
| 3,871,964 | 3/1975 | Huper et al. ...................... 435/181 X |
| 3,957,580 | 5/1976 | Nelson ............................... 435/181 X |
| 3,962,038 | 6/1976 | Kamashima et al. ............ 435/182 X |
| 4,025,391 | 5/1977 | Kamashima et al. ................ 435/182 |
| 4,177,107 | 12/1979 | Kumakura et al. .................. 435/176 |
| 4,193,845 | 3/1980 | Kaetsu et al. ......................... 435/182 |
| 4,194,066 | 3/1980 | Kaetsu et al. ......................... 435/182 |

FOREIGN PATENT DOCUMENTS 50-78640 2/1975 Japan .
51-26285 2/1976 Japan .

*Primary Examiner*—David M. Naff
*Attorney, Agent, or Firm*—Browdy & Neimark

[57] ABSTRACT

Enzymes and/or bacteria cells are immobilized by forming an aqueous mixture of enzymes and/or bacteria cells and a hydrophobic, vitrifiable monomer in an amount of at least 76% by weight of all monomers present, and irradiating the mixture by means of ionizing radiation at a temperature less than −10° C. to polymerize the monomer.

4 Claims, No Drawings

IMMOBILIZATION OF ENZYMES OR BACTERIA CELLS

This is a continuation of application Ser. No. 765,604, filed Feb. 4, 1977, now abandoned.

CROSS-REFERENCE TO OTHER APPLICATION

The U.S. application Ser. No. 763,601 filed Jan. 28, 1977, by the present inventors, now U.S. Pat. No. 4,177,107, corresponding to Japanese Application No. 9702/1976, is related to the present application. In this prior application, the use of a porous adsorbent is critical. But, in the present application, the use of the porous adsorbent is not critical. The present application is characterized by using a hydrophobic, vitrifiable monomer.

BACKGROUND OF THE INVENTION

This invention relates to a process for producing a composition containing insolubilized enzyme and/or insolubilized bacterial cells which can be continuously employed for a long period or which can be repeatedly employed many times in a batch system.

Recently the enzyme industry has become important and has made remarkable progress in producing medicine and food by utilizing enzyme or cells to carry out a variety of reactions.

In the prior art, enzyme reaction was effected by using enzyme solution. In this case, however, after the reaction is completed, the enzyme solution employed in the reaction cannot be reused, because the used enzyme solution contains the resulting reaction product. Therefore, since the enzyme solution employed in the one reaction must be removed from the reaction system, a batch system must be used for the enzyme reaction. In other words, in enzyme reactions using enzyme solution, the maximum effectiveness of the enzyme is not obtained.

U.S. Pat. No. 3,860,490 by Guttag discloses the microorganisms are entrapped in a hydrophilic catalyst. However, the Guttag invention relates to the quick or controlled release of living microorganisms such as bacteria, molds, yeast and viruses or to providing limited contact between the microorganism and an environment on which it acts. The object of the Guttag invention is to store living microorganisms so that they can be released or can act in an appropriate area and/or at an appropriate time. That is, the object of Guttag invention is to keep the microorganisms dry or out of contact with air until use.

U.S. Pat. No. 3,859,169 by O'Driscoll et al discloses that enzymes are provided in gels.

U.S. Pat. No. 3,871,964 by Huper et al discloses that polypeptide such as enzymes are rendered water-soluble by bonding to a cross-linked copolymer.

U.S. Ser. No. 606,209 filed on Aug. 20, 1975 by Kaetsu et al, now U.S. Pat. No. 4,194,066, discloses a process for producing polymer-enzyme composition containing insolubilized enzyme and/or bacterial cells, characterized by irradiating the mixture of a vitrificable monomer and enzyme and/or cells by means of an ionizing radiation at a temperature of less than 0° C. The monomers employed in U.S. Ser. No. 606,209 differ from the monomers employed in the present invention. U.S. Ser. No. 688,081 filed on May 19, 1976 by Kaetsu et al, now U.S. Pat. No. 4,193,845, discloses a similar process. The monomers employed in U.S. Ser. No. 688,081 are water-soluble. The ratio of the activity of the enzyme-polymer composition of U.S. Ser. Nos. 606,209 and 688,081 to the activity of an aqueous solution containing the same enzyme (sometimes referred to as the degree of activity maintained) is as low as 60% or less. In addition, when the enzyme-polymer composition prepared according to U.S. Ser. Nos. 606,209 and 688,081 is used for a long period under severe conditions, the enzyme is likely to be released. Therefore, the enzyme reaction can not continuously be carried out for a long period in a column by using said enzyme-polymer composition.

U.S. Pat. No. 3,962,038 to Kawashima et al discloses that enzymes are entrapped in polymers of acrylamide, bisacrylamide, acrylic acid, sodium acrylate, potassium acrylate and calcium acrylate. The monomers employed in Kawashima et al are in a crystalline state at a temperature less than 0° C. Polymerizability of the crystallizable monomer is lowered at a temperature less than 0° C., because molecular motion of the monomer is restricted by formation of the crystal lattice. When a large total dose of ionizing radiation is used for polymerizing the monomer, there is possiblity of deactivation of the enzyme and the bacterial cells. When the monomer is crystallized at a low temperature, the enzyme and cells can hardly penetrate into the monomer phase. Therefore, enzyme or cells are not firmly entrapped in polymer according to the invention of U.S. Pat. No. 3,962,038.

Japanese Patent Publication (laid open) No. 92446/1973 corresponding to U.S. Ser. No. 225,489 filed on Feb. 11, 1972, now abandoned, discloses an article composed of a water-insoluble, hydrophilic polymer in which an enzyme is entrapped, said polymer being polymers obtained from the monomer selected from the group consisting of hydroxy loweralkyl acrylate, hydro loweralkyl methacrylate, hydroxyloweralkoxy loweralkyl acrylate, hydroloweralkoxy loweralkyl methacrylate, vinylpyrrolidone, acrylamide, methacrylamide, N-loweralkylacrylamide, N-loweralkyl methacrylamide, N-hydroxyloweralkyl acrylamide and N-hydroloweralkyl methacrylamide. However, these monomers disclosed in the above Japanese Publication are water-soluble.

In other words, the prior process for entrapping enzyme or bacterial cells had the disadvantages that the enzyme is likely to release from the polymer. Therefore, compositions containing insolubilized enzyme prepared according to the prior processes can be used only for a short period in a continuous process, and can not be repeatedly used many times in a batch process.

A process for insolubilizing enzyme which comprises mixing enzyme with an water-soluble monomer, and then polymerizing the monomer has been proposed. However, enzyme is unstable to heat, so the polymerization must be carried out at a low temperature. But, the polymerizing reactivity of the monomer is lowered at a low temperature.

SUMMARY OF THE INVENTION

In the prior art, it was thought that enzyme is stable only in an aqueous solution. But, it was found that when an aqueous solution of enzyme is cooled at a temperature less than 0° C., water is crystallized, with the result that the enzyme is liberated from the crystalline water. It was further found that when enzyme is maintained at a temperature less than 0° C., the enzyme is stable in the absence of a buffer solution. Therefore, it was found that the use of a water-soluble monomer is not critical for insolubilizing enzyme in polymer. Of monomers, the number of water-soluble monomers is small. When the use of water-soluble monomers is critical, technique for insolubilizing enzyme or bacterial cells results in being limited.

The present inventors have carried out a variety of experiments for insolubilizing or immobilizing enzyme or bacterial cells by using a variety of monomers. As a result, we found that enzyme and/or bacterial cells can be insolubilized or immobilizing by using a hydrophobic, vitrifiable monomer. We also found that a process for insolubilizing or immobilizing enzyme or cells using a hydrophobic, vitrificable monomer has the same insolubilizing effects as effect of insolubilizing them using a water-soluble monomer. The present invention is based on these discoveries.

Therefore, one object of this invention is to provide compositions containing insolubilized enzyme and/or insolubilzed bacterial cells by using a hydrophobic, vitrifiable monomer.

This invention relates to a process for producing compositions containing insolubilized enzyme and/or insolubilized bacterial cells which comprises mixing an aqueous solution of enzyme and/or an aqueous dispersion of bacterial cells with at least one hydrophobic, vitrifiable monomer and irradiating the resulting mixture by means of an ionizing radiation to polymerize the monomer, characterized in that the irradiation is carried out at a temperature of less than $-10°$ C., preferably from $-100°$ C. to $-25°$ C. and the monomer is selected from the group consisting of a compound having the formula:

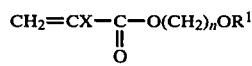
(a)

wherein X is H or methyl, $R^1$ is H or

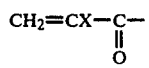

wherein X is as defined above, and n is an integer of 4 to 10;

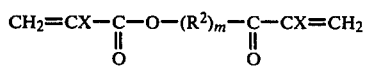
(b)

wherein X is as defined above, $R^2$ is $-CH_2CH_2O-$, $$-\underset{\underset{CH_3}{|}}{CH}-CH_2O-, \text{ or } -CH_2-\underset{\underset{CH_3}{|}}{CHO}-,$$

and m is an integer of 1 to 3;

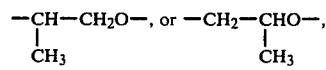
(c)

wherein X is as defined above;

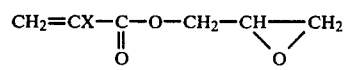
(d)

wherein X is as defined above, $R^3$ is straight chain or branched chain alkylene having from 1 to 10 carbon atoms, and $R^4$ is vinyl or alkyl having from 1 to 10 carbon atoms;

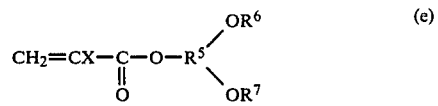
(e)

wherein $R^5$ is alkane ($C_1$ to $C_5$)-yl-ylide, alkylene ($C_1$ to $C_5$) amino, $R^6$ and $R^7$ are independently H, alkyl group having from 1 to 5 carbon atoms, alkylamino group having from 1 to 5 carbon atoms, hydroxyalkyl group having from 1 to 5 carbon atoms, allyl or vinyl;

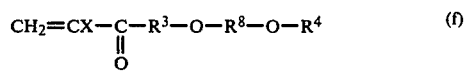
(f)

wherein X, $R^3$ and $R^4$ are as defined above, $R^8$ is the same as $R^3$, $R^3$ and $R^8$ being the same as or different from each other;

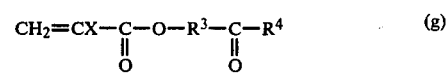
(g)

wherein X, $R^3$ and $R^4$ are as defined above;

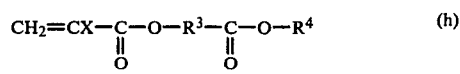
(h)

wherein X, $R^3$ and $R^4$ are as defined above;

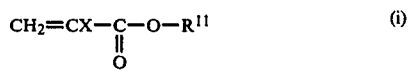
(i)

wherein X is as defined above, and $R^{11}$ is benzyl, toluyl, xylyl, phenyl, furfuryl, naphthyl, phthalyl, cyclohexyl, cyclopentyl, cycloheptyl, cyclobutyl, pyridyl or 3-oxopyrrolidinyl;

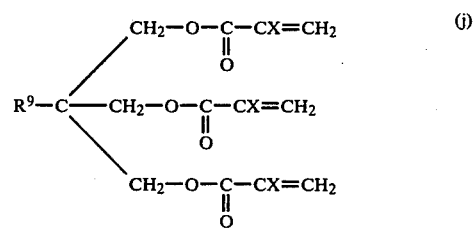
(j)

wherein X is as defined above, and $R^9$ is ethyl or propyl; or

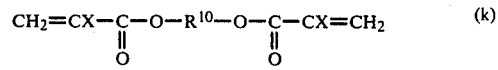
(k)

wherein X is as defined above, and $R^{10}$ is isopropylene, isobutylene, branched chain alkylene having from 1 to 5 carbon atoms,

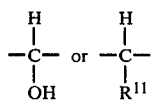

wherein $R^{11}$ is as defined above.

DETAILED DESCRIPTION OF THE INVENTION

By "enzyme reaction" we mean a reaction in which an enzyme or cells are employed as a catalyst, an initiator or a reactant.

By the insolubilization or immobilization of enzyme or cells we mean that the enzyme or cells are held by the polymer so that enzyme or cells may be employed in the enzyme reaction.

The ionizing radiation includes, for example, alpha-rays, beta-rays, electron beam, gamma-rays, X-rays and mixed rays emitted from nuclear reactor. The total dose of irradiation may be in the range of from $10^2$R to $10^7$R, preferably from $10^3$ to $10^6$R; and the dose rate of irradiation may be in the range of from $10^2$R/hr to $10^9$/hr, preferably from $10^3$ to $10^8$R/hr. The irradiation or polymerization is carried out at a temperature of less than $-10°$ C., preferably from $-100°$ C. to $-25°$ C. The irradiation can be carried out even at a temperature of less than $-200°$ C.

Even when a vitrifiable monomer is cooled at a temperature below the melting point thereof, the monomer becomes supercooled, and is not crystallized. It was found that the lower the temperature of vitrifiable monomer in a supercooled state, the more viscous it becomes. It was further found that even when a vitrifiable monomer is maintained at a very low temperature, the polymerizing rate of the monomer is large. When the hydrophobic, vitrifiable monomer employed in the present invention is mixed with an aqueous solution of enzyme, a uniform dispersion is formed. When the dispersion is cooled at a temperature below $-10°$ C., water is crystallized, but the monomer is not crystallized. Therefore, the state in which the monomer suspends enzyme is kept in the dispersion at a temperature below $0°$ C. When such dispersion is irradiated with an ionizing radiation, the composition in which enzyme is firmly entrapped therein results in being formed through the polymerization of monomer at a large polymerizing rate. After polymerization of the monomer, the temperature is raised so that crystals will melt and water is released from the composition, and therefore, a porous composition is formed. Since the reactant for enzyme reaction is likely to penetrate into the porous composition so formed, the enzyme reaction can efficiently be carried out. Furthermore, it is difficult to release insolubilized enzyme contained in the composition from the porous composition thus formed.

At least one adsorbent may be added to the polymerization system. In this case, the enzyme and/or the cells are mixed with the adsorbent, prior to mixing the monomer therewith. When enzyme and/or the cells are mixed with the adsorbent, they are adsorbed onto the surface of adsorbent. The enzyme and/or cells-adsorbing material is very likely to be entrapped in the polymer.

Examples of the adsorbent include molecular sieves, kaolin, alumina, silica gel, activated carbon, Kanuma soil, porous argil, bentonite, acid clay, ion-exchange resin, zinc hydroxide, plastic particles, such as phenol resin particles, polyethylene particles, gelatin particles, amylose, aminopectin, cellulose and its derivatives, agar, collagen, starch and its derivatives, sawdust, cotton, talc, glass beads, silicate, plastic foam particles, flocks, clay, diatomaceous earth and mixtures thereof.

"Kanuma soil" is a soil found in the Kanuma district of Japan. It is sold under the trade name "Kanuma soil" by various companies, and is generally used for gardening.

Examples of the hydrophobic, vitrifiable monomers include pentanediol mono- or di-methacrylate, pentanediol mono- or di-acrylate, hexadiol mono- or di-methacrylate, hexanediol mono- or di-acrylate, heptanediol mono- or di-methacrylate, heptanediol mono- or di-acrylate, octanediol mono- or di-methacrylate, octanediol mono- or di-acrylate, diethyleneglycol dimethacrylate, diethyleneglycol diacrylate, triethyleneglycol dimethacrylate, triethyleneglycol di-acrylate, glycidylacrylate, glycidyl methacrylate, dipropyleneglycoldimethacrylate, dipropyleneglycol diacrylate, tripropyleneglycol dimethacrylate, tripropyleneglycol diacrylate, ethoxyethyl methacrylate, ethoxyethyl acrylate, butoxyethyl methacrylate, butoxyethyl acrylate, isopropoxyethyl methacrylate, isopropoxyethyl acrylate, 2-(2-butoxy ethoxy)ethyl methacrylate, 2-(2-butoxy ethoxy) ethyl acrylate, allyloxymethyl methacrylate, methoxyethyl methacrylate, methoxyethyl acrylate, ethoxypropyl methacrylate, ethoxypropyl acrylate, 2-(2-vinyloxyethoxy) ethyl methacrylate, 2-(2-vinyloxyethoxy) propyl methacrylate, 2-(2-ethoxyethoxy) ethyl methacrylate, acetoxyethyl acrylate, acetoxyethyl methacrylate, acetoxyisobutyl acrylate, acetoxyisopropyl methacrylate, acetylmethyl methacrylate, propionylmethyl methacrylate, acetylmethyl acrylate, propionylmethyl acrylate, butylylmethyl acrylate, butylylmethyl methacrylate, butylacetate acrylate, isobutylacetate acrylate, isopropylacetate acrylate, isopropylacetate methacrylate, butylacetate methacrylate, isobutylacetate benzylmethacrylate, benzyl acrylate, phenyl acrylate, phenyl methacrylate, furfuryl acrylate, furfuryl methacrylate, cyclohexyl acrylate, cyclohexyl methacrylate, cyclopentyl acrylate, cyclopentyl methacrylate, trimethylol propane acrylate, trimethylol propane methacrylate, trimethylol butane acrylate, trimethylol butane methacrylate, 2-ethyl-hexyl acrylate, 2-ethyl-hexyl methacrylate, neopentylglycol diacrylate, neopentylglycol dimethacrylate and mixtures thereof.

Butanediol methacrylate, butanediol acrylate, pentanediol methacrylate, pentanediol acrylate, hexanediol methacrylate, hexanediol acrylate, heptanediol methacrylate, heptanediol acrylate, butanediol dimethacrylate, butanediol diacrylate, pentanediol dimethacrylate, pentanediol diacrylate, hexanediol dimethacrylate, hexanediol diacrylate, heptanediol diacrylate, heptanediol dimethacrylate, ethoxyethyl methacrylate, ethoxyethyl acrylate, methoxyethyl methacrylate, methoxyethyl acrylate, acetoxyethyl acrylate, acetoxyethyl methacrylate, benzyl methacrylate, benzyl acrylate, phenyl acrylate, phenyl methacrylate, cyclohexyl acrylate, cyclohexyl methacrylate, trimethylol propane acrylate, trimethylol propane methacrylate, trimethylol butane acrylate, trimethylol butane methacrylate, 2-ethylhexyl acrylate, 2-ethyl-hexyl methacrylate, neopentylglycol diacrylate, and neopentylglycol dimethacrylate are preferred. One monomer or two or more monomers may be used.

According to the present invention, a variety of enzymes and/or a variety of the bacterial cells can be insolubilized without losing the activity of the enzyme and cells.

The enzymes to be immobilized or to be made insoluble by the present invention include urease, alcohol dehydrogenase, lactic dehydrogenase, malic dehydrogenase, glycose oxidase, diamine oxidase, glycose oxidase-catalase, D-amino acid oxidase, liposidase, uricase, ribonuclease, hexokinase, lipase, alkaline phosphatase, acidic phosphatase, nucleoedase, deoxyribonuclease, α-amylase, β-amylase, glucoamylase, glycoseisomerase, cellulose, hemicellulase, β-glucosidase, invertase, anthoxyanase, narindinase, hesperidinase, β-glucuronidase, hyaluronidase, alkaline protease, semialkaline protease, acidic protease, thermorairin, collagenase, pepsin-pepsinagen, aminopeptidase, rennin, trypsin-trypsinogen, chymotrypsinogen, elastase, enterodinase, acrylate, arginase, L-glutamic acid decarboxylase, L-lysine decarboxylase, and papain.

The bacterial cells to be immobilized or to be made insoluble by the present invention include cells containing the above mentioned enzymes, *Aerobacter aerogenes, Azotobacter vinelandii, Bacillus subtilis, Escherichia coli* and *Micrococcus lysodeikticus*. Other enzymes and bacterial cells can be immobilized or made insoluble according to the present invention.

The blending operation of the enzyme and/or the bacterial cells with the vitrifiable monomer can be carried out by any known method, such as mechanical method.

The proportion of each component in the mixture to be irradiated is not critical. However, conveniently, less than 50 parts by weight of enzyme and/or bacterial cells are used per 100 parts by weight of the monomer, preferably the enzyme and/or the cells in the range of from 5 parts to 30 parts by weight is used. The ratio of water to the monomer may be in the range of from 99:1 to 20:80. In case of using an adsorbent, the ratio of the adsorbent to the monomer may be in the range of from 8:2 to 2:8 by weight, preferably from 6:4 to 4:6.

One enzyme or one kind of bacterial cells may be insolubilized according to the present invention, two or more enzymes or two or more kinds of cells may also be insolubilized. Furthermore, a mixture of enzyme and cells may be insolubilized.

The reason why the polymerization is carried out at a temperature of less than $-10°$ C. is as follows: The enzyme and the bacterial cells are unstable or are likely to be deactivated, so it is necessary that the polymerization of monomer be carried out at such low temperature for insolubilizing the enzyme or cells. Therefore, the use of ionizing radiation as polymerization means is critical to insure polymerization to occur at such low temperature.

A crystallizable monomer is in a crystalline state at a temperature below 0° C. Polymerizability of a crystallizable monomer is lowered at a temperature below 0° C., because molecular motion of the monomer is restricted by formation of the crystal lattice at this temperature. In addition, the crystallizable monomer is not a homogeneous dispersion medium; that is, the mixture of the crystallizable monomer and the enzyme, etc. does not become a homogeneous dispersion in which the enzyme, etc. is uniformly dispersed. Therefore, when the mixture of the crystallizable monomer and the enzyme, etc. is polymerized at a temperature below 0° C., the enzyme, etc. is not firmly entrapped in the resulting polymer.

On the other hand, the hydrophobic, vitrifiable monomer of the present invention is not in a crystalline state at a temperature below $-10°$ C., but is in a supercooled state. Polymerizability of the vitrifiable monomer is very great at a temperature less than $-10°$ C., because the molecular motion of the monomer is not restricted.

Monomers (referred to as second monomer) other than the vitrifiable monomers may be added to the mixture of a hydrophobic, vitrifiable monomer, enzyme and/or bacterial cells and water. The amount of the second monomer may be in the range of from 10% by weight to 30% by weight on the basis of weight of the vitrifiable monomer.

Examples of the second monomers include styrene, methyl methacrylate, methyl acrylate, ethyl methacrylate, ethyl acrylate, butyl methacrylate, butyl acrylate, isobutyl methacrylate, isobutyl acrylate, propyl methacrylate, propyl acrylate, isopropyl methacrylate, isopropyl acrylate, vinyl toluene, alpha-methyl styrene, vinylpyrrolidone, vinylpyridine, acrylic acid, acrylamide, methacrylic acid, methacrylamide, methylol acrylamide, methylene bisacrylamide, vinyl acetate, vinyl butyrate, vinyl propionate, divinylbenzene, dipropargyl maleate, triacrylformal, triallyl cyanurate, isobutyl vinyl ether, diallyl succinate, diallyl phthalate, diallyl maleate, diallyl itaconate, ethylene dimethacrylate, ethylene dimethacrylate, dipropargyl itaconate, triallylisocyanurate, hydroxyethyl methacrylate hydroxypropyl methacrylate, hydroxyethyl acrylate, hydroxypropyl acrylate, itaconic acid, anhydrous maleate and mixtures thereof.

The purpose of adding the second monomer to the polymerization system is to improve strength of the resulting enzyme (cells)-polymer composition, to impart hydrophilic property to the composition to some extent, to lower the cost of the composition, to make the polymer composition more porous, prepare the enzyme or cells-polymer composition having great activity, and to increase stability of holding or insolubilizing the enzyme or bacterial cells in the polymer.

The present invention is further illustrated, but in no way limited, by the following Examples. The percent and parts are based on weight unless otherwise specified.

EXAMPLE 1

Ten parts of a 1% aqueous solution of alpha-amylase was mixed with 40 parts of activated carbon, thereby allowing the carbon to adsorb the amylase. The amylase-adsorbing activated carbon was dispersed in water. Fifty parts of hexanediol methacrylate was added to the dispersion. The resulting dispersion was irradiated with gamma-rays from cobalt 60 at a total dose of $1 \times 10^6$R at temperature of $-24°$ C. to polymerize the monomer. The resulting composition containing enzyme was in the form of flake-like pieces. The flake-like pieces was added to 5 ml of a 1% solution of potato starch paste. The starch was converted to maltose at a temperature of 40° C. for one hour. Therefore, 0.1 N HCl was added to the reaction mixture to discontinue the reaction. From the mixture, a 5 ml sample was withdrawn. The sample was added to 100 ml of solution containing 0.005% $I_2$ and 0.05% KI and shaken. Colorimetric analysis was effected with 10 mm cuvette using wave length of 660 to obtain the activity of the enzyme-polymer composition prepared in this Example.

A control test was carried out by following the above experiment except that the enzyme was used in the state of solution. Similarly, the activity of the enzyme solution was obtained. The ratio of the activity of the enzyme-polymer composition of the present invention obtained in Example 1 to the activity of the enzyme solution was 75%. Even when the enzyme reaction was repeatedly carried out many times using the same composition, the activity of the composition was not lowered.

EXAMPLE 2

Six hundred μg of glucoamylase was dissolved in 0.9 ml of acetic acid buffer solution. The resulting solution was mixed with molecular sieve adsorbent. 0.1 ml of pentanediol methacrylate was added to the mixture. The mixture was irradiated with gamma-rays from cobalt 60 for a total dose of $1 \times 10^6 R$ at temperature of $-78°$ C. to polymerize the monomer. The resulting enzyme-containing composition was in flake-like form. The flake pieces were added to 5 ml of a 1% solution of maltose. The maltose was converted to glucose at a temperature of 40° C. for 30 minutes. The amount of the glucose so formed was determined by quantitative analysis for glucose to obtain the activity of the enzyme-polymer composition prepared in this Example.

A control test was carried out by following the above experiment except that the enzyme was used in the state of solution. Similarly, the activity of the enzyme solution was obtained. The ratio of the activity of the enzyme-polymer composition of the present invention obtained in Example 1 to the activity of the enzyme solution was 70%. Even when the enzyme reaction was repeatedly carried out many times by using the same composition, the activity of the composition was not lowered.

What we claim is:

1. A process for producing a composition containing insolubilized enzyme and/or insolubulized bacterial cells, comprising mixing an aqueous solution of enzyme and/or an aqueous dispersion of bacterial cells with at least one hydrophobic, vitrifiable monomer, said hydrophobic, vitrifiable monomer or monomers comprising more than 76% by weight of all monomers present, and irradiating the resulting mixture by means of an ionizing radiation to polymerize the monomer, the irradiation being carried out at a temperature of less than $-10°$ C., wherein the hydrophobic, vitrifiable monomer or monomers are compounds having a formula selected from the group consisting of:

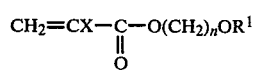 (a)

wherein X is H or methyl, $R^1$ is H or

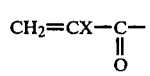

wherein X is as defined above, and n is an integer of 4 to 10;

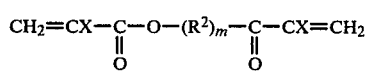 (b)

wherein X is as defined above, $R^2$ is $-CH_2CH_2O-$, $-\underset{\underset{CH_3}{|}}{CH}-CH_2O-$, or $-CH_2-\underset{\underset{CH_3}{|}}{CH}O-$, and m is an integer of 1 to 3;

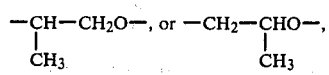 (c)

wherein X is as defined above;

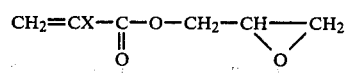 (d)

wherein X is as defined above, $R^3$ is straight chain or branched chain alkylene having carbon from 1 to 10 atoms, and $R^4$ is vinyl or alkyl having carbon from 1 to 10 atoms;

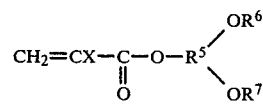 (e)

wherein $R^5$ is alkane ($C_1$ to $C_5$)-yl-ylide, alkylene ($C_1$ to $C_5$) amino, $R^6$ and $R^7$ are independently H, alkyl group having from 1 to 5 carbon atoms, alkylamino group having from 1 to 5 carbon atoms, hydroxyalkyl group having from 1 to 5 carbon atoms, allyl or vinyl;

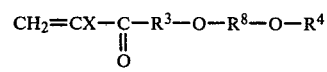 (f)

wherein X, $R^3$ and $R^4$ are as defined above, $R^8$ is the same as $R^3$, $R^3$ and $R^8$ being the same as or different from each other;

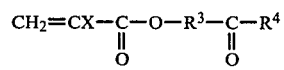 (g)

wherein X, $R^3$ and $R^4$ are as defined above;

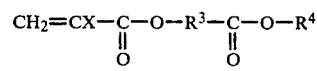 (h)

wherein X, $R^3$ and $R^4$ are as defined above;

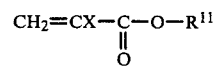 (i)

wherein X is as defined above, and $R^{11}$ is benzyl, toluyl, xylyl, phenyl, furfuryl, naphthyl, phthalyl, cyclohexyl, cyclopentyl, cycloheptyl, cyclobutyl, pyridyl or 3-oxopyrrolidinyl;

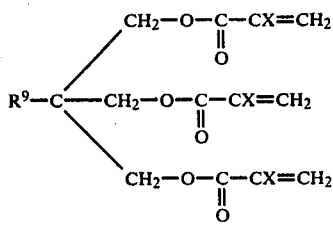

wherein X is as defined above, and $R^9$ is ethyl or propyl; and

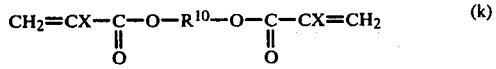

wherein X is as defined above, and $R^{10}$ is isopropylene, isobutylene, branched chain alkylene having from 1 to 5 carbon atoms,

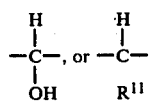

wherein $R^{11}$ is as defined above.

2. The process as defined in claim 1, wherein at least one second monomer other than vitrifiable monomer is an amount of from 10% by weight to 30% by weight is added to the polymerization system on the basis of weight of the vitrificable monomer.

3. The process as defined in claim 1, wherein the irradiation is carried out at a temperature in the range of from $-100°$ C. to $-25°$ C.

4. The process as defined in claim 1, wherein the monomer is selected from the group consisting of butanediol methacrylate, butanediol acrylate, pentanediol methacrylate, pentanediol acrylate, hexanediol methacrylate, hexanediol acrylate, heptanediol methacrylate, heptanediol acrylate, butanediol dimethacrylate, butanediol diacrylate, pentanediol dimethacrylate, pentanediol diacrylate, hexanediol dimethacrylate, hexanediol diacrylate, heptanediol diacrylate, heptanediol dimethacrylate, ethoxyethyl methacrylate, ethoxyethyl acrylate, methoxyethyl methacrylate, methoxyethyl acrylate, acetoxyethyl acrylate, acetoxyethyl methacrylate, benzyl methacrylate, benzyl acrylate, phenyl acrylate, phenyl methacrylate, cyclohexyl acrylate, cyclohexyl methacrylate, trimethylol propane acrylate, trimethylol propane methacrylate, trimethylol butane acrylate, trimethylol butane methacrylate, 2-ethylhexyl acrylate, 2-ethyl-hexyl methacrylate, neopentylglycol diacrylate, neopentylglycol dimethacrylate and mixtures thereof.

* * * * *